United States Patent [19]

Creuzet et al.

[11] 4,333,930
[45] Jun. 8, 1982

[54] ORTHOARYLIDENEAMINOPHENETHYLAMINES AND PHARMACEUTICAL COMPOSITIONS

[75] Inventors: Marie-Helene Creuzet, Bordeaux; Claude Feniou, Pessac; Francoise Guichard, Bordeaux; Gisele Prat, Talence, all of France

[73] Assignee: Laboratoires Sarget, Merignac, France

[21] Appl. No.: 237,277

[22] Filed: Feb. 23, 1981

[30] Foreign Application Priority Data

Feb. 21, 1980 [FR] France ................................. 80 03774

[51] Int. Cl.³ .................. A61K 31/535; A61K 31/36; C07D 413/06; C07D 317/58
[52] U.S. Cl. .......................... 424/248.51; 424/248.53; 424/248.56; 424/250; 424/263; 424/267; 424/274; 424/275; 424/278; 424/282; 424/285; 424/319; 424/330; 542/422; 542/423; 564/271; 564/272; 564/274; 564/275; 564/276; 562/440
[58] Field of Search ................ 542/422, 423; 564/271, 564/272, 274, 275, 276; 562/440; 424/248.51, 248.53, 248.56, 250, 263, 267, 274, 275, 278, 282, 285, 319, 330

[56] References Cited

FOREIGN PATENT DOCUMENTS 2644M 7/1964 France .
6923M 5/1969 France .

OTHER PUBLICATIONS

Krapcho et al., *J. Med. Chem.*, vol. 9 (1966) pp. 809-812.
Pillon et al., *Chem Abstracts*, vol. 67 (1967) No. 32486n.

*Primary Examiner*—Robert W. Ramsuer
*Attorney, Agent, or Firm*—Oblon, Fisher, Spivak, McClelland & Maier

[57] ABSTRACT

Compounds, exhibiting central nervous system activity, of the formula

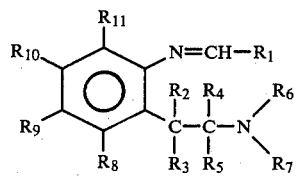

wherein
$R_1$ is phenyl which is unsubstituted or substituted by at least one member selected from the group consisting of halogen, $CF_3$, $C_1$-$C_4$ alkyl, $C_1$-$C_4$ alkoxy and COOH, or
$R_1$ is

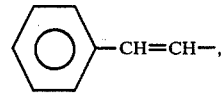

or
$R_1$ is a heterocycle selected from the group consisting of

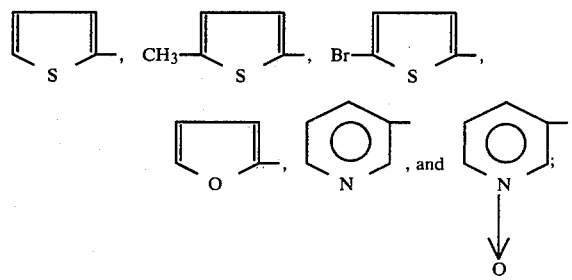

$R_2$, $R_3$, $R_4$ and $R_5$, which may be identical or different, are H or $CH_3$;
$R_6$ and $R_7$, which may be identical or different, are $C_1$-$C_6$ alkyl, which may be straight-chained or branched, or
$R_7$ can be H when $R_6$ is a branched-chain alkyl, or
$R_6$ and $R_7$ can form, with the nitrogen to which they are bonded, a heterocycle selected from the group consisting of

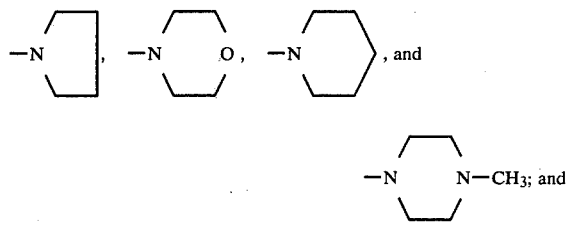

$R_8$, $R_9$, $R_{10}$ and $R_{11}$, which may be identical or different, are H, halogen, $CF_3$, hydroxy or $C_1$-$C_4$ alkoxy, or two contiguous members of $R_8$, $R_9$, $R_{10}$ and $R_{11}$ may together form a chain $-O-(CH_2)_n-O-$, where n=1 or 2, or a chain $-O-CH_2-O-CH_2-$;
and pharmaceutically acceptable addition salts thereof are disclosed, along with a method of producing the same, and pharmaceutical compositions comprising the same.

7 Claims, No Drawings

ORTHOARYLIDENEAMINOPHENETHYLAMINES AND PHARMACEUTICAL COMPOSITIONS

BACKGROUND OF THE INVENTION

1. Field of the Invention

The present invention relates to new therapeutic derivatives used, particularly, for their effect on the central nervous system and to their method of preparation.

2. Description of the Prior Art

There is little mention of orthoaminophenethylamines in the scientific literature. There are, however, the following references: 2-dimethylaminoethyl-aniline, synthesized by J. Krapcho et al, J. Med. Chem. 1966, 809–812, as an intermediate in the synthesis of cinnamanilides having hypotensive and antiserotonin properties; 2-aminoethyl-4,5-dihydroxy-aniline described in French Medical Patent No. 2644 for its antihypertensive properties; and dihalogeno-amino phenethylamines described in French Medical Patent No. 6923.

A need continues to exist, however, for new therapeutic products for the central nervous system with antidepressive, anxiolytic and analgesic properties.

SUMMARY OF THE INVENTION

Accordingly, one object of the invention is to provide therapeutic products for treatment of the central nervous system with antidepressive, anxiolytic and analgesic properties.

A further object of the invention is to provide a method of making such therapeutic products.

An additional object of the invention is to provide pharmaceutically acceptable compositions containing such therapeutic products.

Briefly, these objects and other objects of the invention as hereinafter will become more readily apparent can be attained by providing a compound of the formula (I)

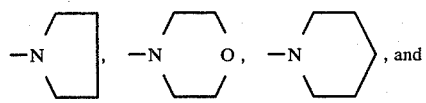

wherein
R$_1$ is phenyl which is unsubstituted or substituted by at least one member of the group consisting of halogen, CF$_3$, C$_1$-C$_4$ alkyl, C$_1$-C$_4$ alkoxy and COOH, or
R$_1$ is

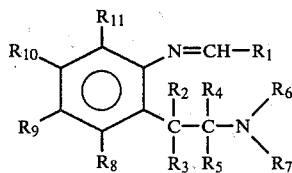

or
R$_1$ is a heterocycle selected from the group consisting of

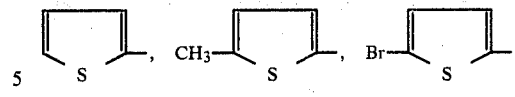

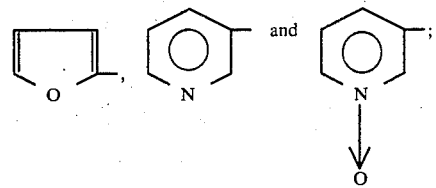

R$_2$, R$_3$, R$_4$ and R$_5$, which may be identical or different, are H or CH$_3$;
R$_6$ and R$_7$, which may be identical or different, are C$_1$-C$_6$ alkyl, which may be straight-chained or branched, or
R$_7$ can be H when R$_6$ is a branched-chain alkyl, or
R$_6$ and R$_7$ can form, with the nitrogen to which they are bonded, a heterocycle selected from the group consisting of

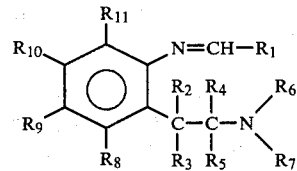

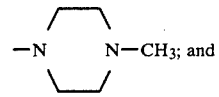

R$_8$, R$_9$, R$_{10}$ and R$_{11}$, which may be identical or different, are H, halogen, CF$_3$, hydroxy or C$_1$-C$_4$ alkoxy, or two contiguous members of R$_8$, R$_9$, R$_{10}$ and R$_{11}$ may together form a chain —O—(CH$_2$)$_n$—O—, where n=1 or 2, or a chain —O—CH$_2$—O—CH$_2$—; or pharmaceutically acceptable addition salts thereof.

DETAILED DESCRIPTION OF THE PREFERRED EMBODIMENTS

The compounds of the invention are characterized by the following formula (I)

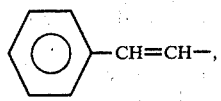

wherein
R$_1$ is phenyl which is unsubstituted or substituted by at least one member of the group consisting of halogen, CF$_3$, C$_1$-C$_4$ alkyl, C$_1$-C$_4$ alkoxy and COOH, or
R$_1$ is

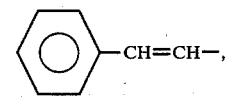

or

R$_1$ is a heterocycle selected from the group consisting of

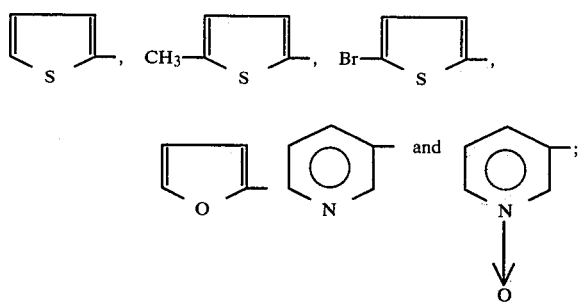

R$_2$, R$_3$, R$_4$ and R$_5$, which may be identical or different, are H or CH$_3$;

R$_6$ and R$_7$, which may be identical or different, are C$_1$–C$_6$ alkyl, which may be straight-chained or branched, or R$_7$ can be H when R$_6$ is a branched chain alkyl, or R$_6$ and R$_7$ can form, with the nitrogen to which they are bonded, a heterocycle selected from the group consisting of

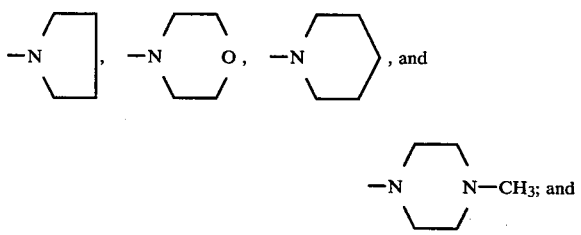

R$_8$, R$_9$, R$_{10}$ and R$_{11}$, which may be identical or different, are H, halogen, CF$_3$, hydroxy or C$_1$–C$_4$ alkoxy, of two contiguous substituents may together form a chain —O—(CH$_2$)$_n$—O—, where n=1 or 2, or a chain —O—CH$_2$—O—CH$_2$—.

These imines, derived from ortho amino phenethylamines, exercise psychotropic action allowing them to be used as medicines with anxiolytic and antidepressive activities. The structure of these compounds is very different from the structure of products habitually used in this area.

The compounds of this invention are obtained in a general manner by the reaction of an amine having the formula II and an aldehyde having the formula III, according to the reaction scheme:

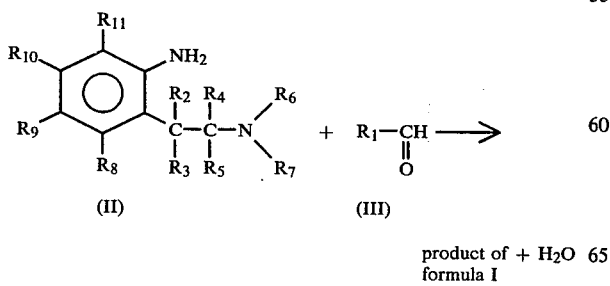

product of + H$_2$O
formula I

The amines of formula II and the aldehydes of formula III are obtained by conventional procedures, depending on the substituents R$_2$ to R$_{11}$ and R$_1$, as are known to those of ordinary skill in the art.

The compounds of formula I exhibit pharmacological properties characterized by an analgesic activity; an antidepressive activity, non-IMAO; an anxiolytic activity and an anticholinergic activity. These activities are manifested in the whole range of doses up to toxic levels. The products forming the object of this invention can be used, e.g., in the treatment of depressive states of various etiologies of anxiety, in the treatment of states of anxiety observed in the course of certain psychiatric or organic diseases, in the treatment of the depressive component and of akinetic manifestations of Parkinson's disease; with children, they make it possible to treat insomnia, nervous tics, stuttering, enuresis, nightmares; with the aged, they are used for the treatment of insomnia, difficulties relating to surroundings, and psychiatric involution problems; they may also be used in preparing for small interventions and for the treatment of certain pains.

The compounds of formula I can be admixed with any pharmaceutically acceptable diluent to form, e.g., tablets, capsules, drinkable drop or injectable solutions.

Additionally, the pharmaceutically acceptable acid addition salts, e.g., chlorhydrates, citrates or benzilates, may be used in lieu of the free base compounds of formula I.

Having generally described this invention, a further understanding can be obtained by reference to certain specific examples which are provided herein for purposes of illustration only and are not intended to be limiting unless otherwise specified.

EXAMPLE I

Synthesis of the 6-dimethylaminoethyl N-(-3-pyridylidene)-1,3-benzodioxole-5-ylamine (formula I: R$_1$=

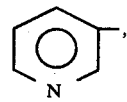

R$_2$=R$_3$=R$_4$=R$_5$=H, R$_6$=R$_7$=CH$_3$, R$_8$=R$_{11}$=H, R$_9$—R$_{10}$=—O—CH$_2$—O—) and of its benzilate (COR 01 170).

1. Synthesis of the 6-(2-N,N-dimethylaminoethyl)-1,3-benzodioxole-5-ylamine 400 cm$^3$ of thionyl chloride are added to 120 g of 1,3-benzodioxole-5-acetic acid. The mixture is kept overnight with being stirred at room temperature. The excess thionyl chloride is evaporated. The chloride of the 1,3-benzodioxol-5-acetic acid is distilled (B.Pt. 0.2 mm Hg=100° C.). Yield 92%.

A volume of 100 cm$^3$ of dimethylamine is brought to 0° C. 100 g of the chloride of 1,3-benzodioxol-5-acetic acid are added very slowly with stirring.

The mixture is kept with stirring for one hour and then filtered. After evaporation and distillation of the filtrate, one obtains the dimethylamide of 1,3-benzodioxol-5-acetic acid. B.Pt. 0.3 mm Hg=145° C. Yield 90%.

9 g of LiAlH$_4$ are poured into a 2 liter container (Grignard). 400 cm$^3$ of very dry ethyl ether are added and the mixture is brought to reflux. A solution of 24 g of the dimethylamide in 300 to 400 cm³ of dry ethyl ether is poured in drop-by-drop. All of this is kept at reflux being stirred for one hour. After refrigeration, 150 cm³ of ethyl acetate are poured in drop-by-drop, then 300 cm³ of water saturated with sodium sulfate. After decantation the ethereal phase is evaporated and the derived dimethylamine is distilled. B.Pt. 0.1 mm Hg=95° C. Yield 89%.

While maintaining the temperature between 25° and 30° C., 0.1 mole of the amine (19.3 g) is stirred drop-by-drop into 200 cm³ of nitric acid (d=1.2). The mixture is kept in agitation for 2 hours. The precipitation of the derived nitro compound is eventually primed by a little ice. The derived ortho nitro compound is washed to neutrality then dried under P₂O₅. M.Pt.=174° C. Yield 98%.

40 g of this nitro product are suspended in 1.8 liter of methanol then reduced in a hydrogen atmosphere in the presence of Raney nickel at room temperature. After filtration and evaporation of the solvent, the 6-N,N-dimethylaminoethyl-1,3-benzodioxole-5-ylamine is distilled.

B.Pt. 0.06 mm Hg=125° C. Yield 70%.

2. Formation of the imine

A mixture comprising 0.025 mole of the previously prepared amine (5.25 g), 0.05 mole of pyridine-3-carboxaldehyde (5.35 g) and 100 cm³ of benzene is heated to 120° C. while being stirred. The water formed in the course of the reaction is eliminated with the help of a Dean and Stark trap. When 0.025 mole of water has been collected (0.45 cm³), the benzene is evaporated, the excess aldehyde is distilled and then the imine. B.Pt. 0.02 mm Hg=165° C. M.Pt.=66° C. Yield=67%.

3. Salification

To a solution of 0.01 mole of imine in 400 cm³ of anhydrous ethyl ether, refrigerated to 0° C., is added slowly a solution of 0.01 mole of benzilic acid in 300 cm³ of anhydrous ethyl ether. The precipitate is filtered and quickly dried. One obtains the benzilate of the 6-dimethylaminoethyl N-(pyridylidene-3)-1,3-benzodioxole-5-ylamine (COR 01 170). M.Pt.=130° C. The citrate of this amine (COR 01 201 (hygroscopic)) is prepared in the same way.

EXAMPLE II

Several imines derived from the 6-(2-N,N-dimethylaminoethyl)-1,3-benzodioxole-5-ylamine are prepared according to the procedure described in Example I. They consist of the products of formula I wherein $R_2=R_3=R_4=R_5=H$, $R_6=R_7=CH_3$, $R_8=R_{11}=H$, $R_9\text{-}R_{10}=\text{—O—CH}_2\text{—O}$ and

| | | | |
|---|---|---|---|
| $R_1 =$ ⟨thienyl⟩, | benzilate, | COR 01 151, M.Pt. = 139° C. | |
| $R_1 =$ ⟨thienyl⟩, | chlorhydrate, | COR 01 163, M.Pt. = 186° C. | |
| $R_1 =$ Me-⟨thienyl⟩, | benzilate, | COR 01 169, M.Pt. = 151° C. | |
| $R_1 =$ ⟨thienyl⟩, | free base, | COR 01 171, M.Pt. = 117° C. | |
| $R_1 =$ ⟨O⟩-CH=CH—, | citrate, | COR 01 176, M.Pt. = 144° C. | |
| $R_1 =$ ⟨thienyl⟩, | citrate | COR 01 179, M.Pt. = 171° C. | |
| $R_1 =$ Br-⟨thienyl⟩, | citrate, | COR 01 181, M.Pt. = 171° C. | |
| $R_1 =$ ⟨pyridyl N→O⟩, | citrate, | COR 01 203, hygroscopic | |
| $R_1 =$ Me-⟨O⟩-, | citrate, | COR 01 206, M.Pt. = 176° C. | |
| $R_1 =$ Cl-⟨O⟩-, Cl | citrate | COR 01 207, hygroscopic | |
| $R_1 =$ Cl-⟨O⟩-, | citrate | COR 01 208, hygroscopic | |
| $R_1 =$ ⟨O⟩-, | citrate | COR 01 209, M.Pt. = 178° C. | |
| $R_1 =$ MeO-⟨O⟩-, | citrate, | COR 01 210, hygroscopic | |

EXAMPLE III

Synthesis of the 6-(2-N-piperidinoethyl) N-(thienylidene-2)-1,3-benzodioxole-5-ylamine (formula I, $R_1$ 32

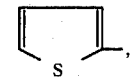

$R_2=R_3=R_4=R_5=H$, $R_6\text{-}R_7=(CH_2)_5$, $R_8=R_{11}=H$, $R_9\text{-}R_{10}=\text{—O—CH}_2\text{—O—}$) and of its benzilate (COR 01 175).

0.25 mole (49.5 g) of the chloride of 1,3-benzodioxol-5-acetic acid are poured drop-by-drop at room temperature into a mixture of 0.5 mole of piperidine, 0.5 mole of triethylamine, 400 cm³ of benzene. The mixture is stirred constantly for one hour at room temperature. After filtration, the filtrate is washed with water, evaporated and distilled (B.Pt. 0.15 mm Hg=175° C.).

A mixture of 0.26 mole of LiAlH₄ (10 g) in suspension in 400 cm³ of dry ethyl ether is brought to reflux. 0.13 mole of the previously prepared amide (33 g) dissolved in 300 cm³ of tetrahydrofuran is poured in drop-by-drop. The mixture is kept at reflux for one hour. After refrigeration, 200 cm³ of ethyl acetate is added drop-by-drop, then 300 cm³ of a saturated aqueous solution of sodium sulfate. The ethereal phase is washed to neutrality; the solvent is evaporated; the amine is distilled (B.Pt. 0.02 mm Hg=110° C.). 0.12 mole of 5-piperidinoethyl-1,3-benzodioxole thus prepared is poured drop-by-drop while being stirred into 240 cm³ of nitric acid (d=1.2) while maintaining the temperature between 25° and 30° C. The mixture is constantly stirred for one hour. After refrigeration, the derived nitro compound precipitates. It is filtered, washed with a little water and dried. M.Pt.=207° C. Yield 76%.

25 g of the derived nitro compound are suspended in 2 liters of methanol then reduced in a hydrogen atmosphere in the presence of Raney nickel. After filtration and evaporation of the solvent, the amine is distilled. B.Pt. 0.05 mm Hg=160° C. Yield 64%.

The mixture of 6.2 g of amine (0.025 mole), 5.6 g of thiophene-2-carboxaldehyde (0.05 mole) and 50 cm³ of benzene is brought to reflux. The water formed in the course of the reaction is eliminated with the help of a Dean-Stark trap. The excess aldehyde is distilled and the imine is recrystallized in petroleum ether. M.Pt.=62° C. To a solution containing 0.1 mole of the imine in dry ethyl ether, refrigerated to 0° C., is added drop-by-drop 0.1 mole of benzilic acid dissolved in dry ethyl ether. The benzilate is separated by filtration then dried. M.Pt.=162° C.

EXAMPLE IV

The method described in Example III allows synthesis of the derivatives of formula I with $R_2=R_3=R_4=R_5=H$, $R_9-R_{10}=O-CH_2-O$, $R_8=R_{11}=H$ and one hour at room temperature then heated to 70° C. for 4 hours. The alcohol is evaporated. After refrigeration, the residue is dissolved in an aqueous chlorhydric solution. The product that has not reacted is extracted with ether. The acid solution is alkalized and extracted with ether. The ethereal phase is washed to neutrality, dried, and evaporated. The N,N-dimethyl-2-nitrophenethyl amine is separated by distillation. B.Pt. 0.2 mm Hg=95° C. Yield 81%. This amine is dissolved in methanol and reduced in a hydrogen atmosphere in the presence of Raney nickel. When the reaction is finished the mixture is filtered, evaporated then distilled to produce the 2-(2-N,N-dimethylaminoethyl)aniline. B.Pt. 0.1 mm Hg=85°–90° C. Yield 89%. A mixture containing 0.05 mole of the previously prepared aniline (8.2 g), 0.10 mole of cinnamaldehyde (13.2 g)+50 cm³ of benzene is heated to 120° C. The water formed in the course of the

| $R_1 =$ | | $R_6 + R_7 = -(CH_2)_4-$, benzilate, | COR 01 173, M.Pt. = 140° C. |
|---|---|---|---|
| $R_1 =$ | | $R_6 + R_7 = -(CH_2)_5-$, benzilate, | COR 01 174, M.Pt. = 156° C. |
| $R_1 =$ | | $R_6 + R_7 = -CH_2CH_2OCH_2CH_2-$, citrate, | COR 01 180, M.Pt. = 179° C. |
| $R_1 =$ | | $R_6 + R_7 = -(CH_2)_4-$, citrate, | COR 01 186, M.Pt. = 187° C. |
| $R_1 =$ | | $R_7 = H, R_6 = tBu$, citrate, | COR 01 195, hygroscopic |
| $R_1 =$ | —CH=CH—, | $R_6 + R_7 = -(CH_2)_4-$, citrate, | COR 01 200, hygroscopic |
| $R_1 =$ | | $R_6 + R_7 = -(CH_2)_5-$, citrate, | COR 01 202, M.Pt. = 196° C. |
| $R_1 =$ | | $R_6 + R_7 = -CH_2CH_2OCH_2CH_2-$, citrate, | COR 01 204, M.Pt. = 210° C. |

EXAMPLE V

Synthesis of the N-cinnamylidene 2-(2-N,N,-dimethylaminoethyl)aniline (formula 1, $R_1=$

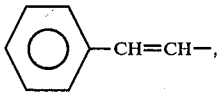—CH=CH—, $R_2=R_3=R_4=R_5=H$, $R_6=R_7=CH_3$, $R_8=R_9=R_{10}=R_{11}=H$) and of its citrate (COR 01 185).

50 g of o-nitrophenethylalcohol are added drop-by-drop to 425 cm³ of bromhydric acid (48%). The mixture is heated and stirred for 3 hours at 100° C. After refrigeration, it is submitted to an extraction by ether. The ethereal phase is washed with water and dried with Na₂SO₄, then the solvent is eliminated by evaporation. After refrigeration to −30° C., the 2-(2-bromoethyl)-1-nitrobenzene crystallizes, it is purified by washing in ethanol. M.Pt.<50° C. Yield 82%. 56 g of this derivative are dissolved in 700 cm³ of ethanol. This solution is added drop-by-drop to 100 cm³ of dimethylamine refrigerated to 0° C. The mixture is constantly stirred for reaction is received in a Dean-Stark trap. When 0.05 mole of water (0.9 cm³) has been received, the benzene is evaporated and the residue is distilled. B.Pt. 0.025 mm Hg=158° C. 8.63 g (0.031 mole) of the so-prepared imine are dissolved in anhydrous ethyl ether. After refrigeration to 0° C., 5.95 g of citric acid dissolved in the minimum of anhydrous methanol are poured in drop-by-drop. An oily product separates. After decantation, ethyl ether is readded to the oily residue. Refrigeration to −40° C. allows the crystallization to begin; the citrate is separated by filtration and dried; hygroscopic product.

EXAMPLE VI

The following derivatives were prepared in the same manner: formula I with $R_2=R_3=R_4=R_5=H$, $R_8=R_9=R_{10}=R_{11}=H$, $R_1=$

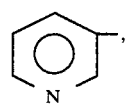

$R_6=R_7=CH_3$, citrate (COR 01 184), hygroscopic product; $R_1=$

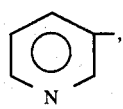

$R_6+R_7=$ $$-CH_2CH_2-\underset{\underset{CH_3}{|}}{N}-CH_2CH_2-,$$

citrate (COR 01 205), hygroscopic product.

EXAMPLE VII

Synthesis of 2-(2-N,N-dimethylamino-1-methylethyl)-N-pyridylidene-3 aniline; (formula I with $R_1=$

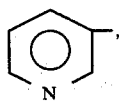

$R_2=R_4=R_5=H$, $R_3=CH_3$, $R_8=R_9=R_{10}=R_{11}=H$; and of its citrate (COR 01 123).

The mixture consisting of 50 g of o-nitrophenyl acetic acid, 500 cm³ of methanol, and 4 cm³ of concentrated sulfuric acid is heated to reflux of methanol overnight. After refrigeration and neutralization by soda dissolved in methanol, the alcohol is evaporated, then the residue is dissolved in ethyl ether. The ethereal phase is washed with diluted soda solution then with water and then dried and evaporated to dryness. To a suspension of 0.65 mole of NaH (16 g) in 250 ml of triamide of hexamethyl phosphoric acid (HMPT) is stirred drop-by-drop 0.35 mole of orthonitrophenylmethyl acetate (103 g) dissolved in 20 ml of HMPT, then 0.53 mole of ethyl iodide (76 g). The mixture is constantly stirred at room temperature overnight then poured into ice. To it is added 250 cm³ of HCl diluted ½. After benzene extraction, the benzene phases are washed to neutrality, dried, evaporated and double distilled. B.Pt. 0.03 mm Hg=92° C. 24 g of methyl-2-orthonitrophenyl propionate are dissolved in 300–400 cm³ of anhydrous ethanol. 15 g of NaBH₄ are added to the solution which is kept at reflux and stirred for 17 hours. After refrigeration, the excess NaBH₄ is destroyed by acetic acid. The alcohol is evaporated; water and ethyl ether are added to the evaporation residue. The ethereal phase is washed in water, dried on Na₂SO₄ and distilled. B.Pt. 0.03 mm Hg=105°–110° C. 27 g 2-(orthonitrophenyl)propanol are added to 220 cm³ of 48% bromhydric acid. The mixture is heated to 100° C. for 6 hours and extracted with ether. The ethereal phase is washed with water, dried on Na₂SO₄, evaporated and distilled. B.Pt. 0.02 mm Hg=112° C. Yield 90%. A solution of 35 g of the 1-bromo-2-(o-nitrophenyl)propane diluted in 100 ml of absolute ethanol is added to 60 cm³ of dimethylamine refrigerated to 0° C. The mixture is heated to 70° C. for 20 hours. The alcohol is evaporated. The residue is dissolved in a solution of dilute chlorhydric acid and extracted twice with ethyl ether. The acid, aqueous phase is alkalized, chloroform extracted, dried on Na₂SO₄, evaporated and distilled; B.Pt. 0.2 mm Hg=90° C. 11.5 g of the N,N-dimethyl-2-(o-nitrophenyl)propylamine in solution in 500 cm³ of methanol are reduced in the presence of Raney nickel in a hydrogen atmosphere. When the reaction is complete, the mixture is filtered, the filtrate evaporated and the residue distilled; B.Pt. 0.1 mm Hg=82° C. The mixture comprising 0.02 mole of the 2-(2-N,N-dimethylamino-1-methylethyl)aniline, 0.04 mole of nicotinaldehyde, and 120 cm³ of anhydrous benzene is heated to 120° C. The water formed in the course of the reaction is eliminated with the help of a Dean-Stark trap. The benzene is evaporated, then the excess nicotinaldehyde is distilled. The imine is obtained by distillation. B.Pt. 0.03 mm Hg=135° C. 4.16 g of the imine (0.015 mole) are dissolved in a liter of anhydrous ethyl ether. After refrigeration to −5° C., one adds, drop-by-drop, 2.88 g of citric acid (0.015 mole) dissolved in the minimum of anhydrous methanol. The citrate is obtained after filtration and drying by vacuum pumping at 40° C. Hygroscopic product.

EXAMPLE VIII

Synthesis of 2-(2-N,N-dimethylamino-2-methylethyl)-N-pyridylidene-3 aniline (formula I with $R_1=$

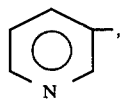

$R_2=R_3=R_4=H$, $R_5=CH_3$, $R_6=R_7=CH_3$, $R_8=R_9=R_{10}=R_{11}=H$) and of its citrate (COR 01 214).

A solution of 78 g (0.6 mol) of ethyl acetoacetate in 150 ml of hexamethylphosphorotriamide (HMPT) is added drop-by-drop to 21.6 g (0.9 mole) of NaH in 110 ml of HMPT. To this mixture are subsequently added drop-by-drop 84.6 g (0.06 mole) of o-fluoronitrobenzene in 100 ml of HMPT. The mixture is kept overnight at room temperature. It is then poured into ice and stirred. After the addition of 300 cm³ of HCl diluted to ½, it is benzene extracted, washed with water and then distilled. B.Pt. 0.05 mm Hg=110° C. 50 g of the ethyl-2-(o-nitrophenyl)-3-oxobutyrate are heated to 120° C. while being stirred in a liter of chlorhydric acid diluted to ½. After refrigeration, chloroform extraction, water washing, drying on Na₂SO₄, and evaporation, the methyl (o-nitrobenzyl) ketone is distilled. Yield 40–50%. A mixture comprising 26 g of this ketone, 300 cm³ of absolute ethanol, 13 g of NaBH₄ is constantly stirred for two hours. The excess NaBH₄ is destroyed by CH₃COOH. The ethanol is eliminated by evaporation. After ether extraction, washing the ethereal phase with water, drying and evaporation, the 1-(o-nitrophenyl)-2-propanol is separated by distillation. B.Pt. 0.03 mm Hg=105° C. M.Pt. <50° C. A mixture containing 15 g of this alcohol in 120 cm³ of 48% bromhydric acid is heated for 2 hours at 100° C. After refrigeration and ether extraction, the ethereal phase is washed with water, dried and evaporated. The 2-bromo-1-(o-nitrophenyl)propane is separated by distillation. B.Pt. 0.02 mm Hg=120° C. Yield 86%. A mixture containing 11 g of this product, 40 cm³ of dimethylamine, and 20 cm³ of absolute ethanol is heated overnight at 70° C. in an autoclave. The solvents are evaporated. The residue is dissolved in a diluted HCl solution and ethyl ether extracted twice. The acid aqueous phase is alkalized, chloroform extracted, dried on sodium sulfate, evaporated and distilled. B.Pt. 0.2 mm Hg=90° C. 9.5 g of N,N-dimethyl-1-o-nitrophenylpropyl-2-amine thus prepared are dissolved in 500 cm³ of methanol and reduced in a hydrogen atmosphere in the presence of Raney nickel. After filtration and evaporation of the filtrate, the 2-(2-N,N-dimethylamino-2-methylethyl)aniline is separated by distillation. The mixture made of 5.9 g of this amine (0.033 mole), 0.066 mole of nicotinic aldehyde and 150 cm³ of anhydrous benzene is heated to 120° C. The water formed in the course of the reaction is eliminated with the help of a Dean-Stark trap. The benzene is evaporated. Distillation makes it possible to eliminate the excess nicotinic aldehyde and then to recover the imine. 7.37 g of this (0.027 mole) are placed in solution in 1.5 liter of anhydrous ethyl ether. To this solution, refrigerated between −5° and −10° C., are added drop-by-drop 5.18 g of citric acid (0.027 mole) dissolved in the minimum of anhydrous methanol. The citrate is obtained by filtration and vacuum drying at 40° C. Hygroscopic product.

EXAMPLE IX

Synthesis of N-6-(2-N,N-dimethylaminoethyl)-1,3-benzodioxol-5-yl-2-formimidoylbenzoic acid, internal salt; (formula I: $R_1 =$

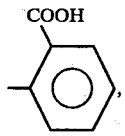, $R_2=R_3=R_4=R_5=H$, $R_6=R_7=CH_3$, $R_8=R_{11}=H$, $R_9+R_{10}=-O-CH_2-O-$); COR 01 142.

7.5 g of phthalaldehydic acid (0.05 mole) are placed in suspension in 800 cm³ of benzene. The mixture is heated to reflux of benzene. One adds to it 0.055 mole of 6-(N,N-dimethylaminoethyl)-1,3-benzodiopole-5-ylamine (11.4 g) diluted in 200 cm³ of benzene. The water formed in the course of the reaction is eliminated with the help of a Dean-Stark trap. The precipitate is separated by cold filtration, washed with benzene and vacuum dried. Yield 70%. M.Pt.=204° C.

The products of the present invention have the following physicochemical characteristics:

1. Nuclear magnetic resonance spectrum, internal standard (TMS)

COR 01 142, methyl ester prepared by diazotation, solvent CDCl₃

2.3 ppm 6 protons; signlet; $N(CH_3)_2$
2.2–3.2 ppm 4 protons; massive complex; $-CH_2-CH_2-N$
3.9 ppm 3 protons; singlet; $CH_3-O$
5.9 ppm 2 protons; singlet; $O-CH_2-O$
6.7 ppm 2 protons; 2 singlets; aromatic protons (benzodioxolyl)
7.2–8.4 ppm 4 protons; massive complex; aromatic protons (benzylidene)
9.1 1 proton; singlet; $-N=CH-$ COR 01 151 solvent DMSO-D6

2.7 ppm 6 protons; singlet; $N(CH_3)_2$
2.9–3.2 ppm 4 protons; massive complex; $-CH_2-CH_2-N$
6.0 ppm 2 protons; singlet; $O-CH_2-O$
6.7–7.8 ppm 15 protons; massive complex; aromatic protons
7.5–9 ppm 2 protons; spread peak; labile protons exchangeable with D₂O
8.8 ppm 1 proton; singlet; $-N=CH-$ COR 01 163 solvent DMSO-D6

2.8 ppm 6 protons; singlet; $N(CH_3)_2$
3.0–3.4 ppm 4 protons; massive complex; $-CH_2-CH_2-N$
6.0 ppm 2 protons; singlet; $-O-CH_2-O-$
6.8–8.0 ppm 5 protons; massive complex; aromatic protons
8.8 ppm 1 proton; singlet; $-N=CH-$
11 ppm 1 proton; singlet; labile proton exchangeable with D₂O COR 01 169 solvent CDCl₃

2.5 ppm 3 protons; singlet; thienyl-$CH_3$
2.7 ppm 6 protons; singlet; $N(CH_3)_2$
2.8–3.2 ppm 4 protons; massive complex; $-CH_2-CH_2-N$
5.9 ppm 2 protons; singlet; $-O-CH_2-O-$
6.4–7.8 ppm 14 protons; massive complex; aromatic protons
8.3 ppm 1 proton; singlet; $-N=CH-$
8.5–10 ppm 2 protons; spread peak; labile protons exchangeable with D₂O COR 01 170 solvent CDCl₃

2.6 ppm 6 protons; singlet; $N(CH_3)_2$
2.9–3.2 ppm 4 protons; massive complex; $-CH_2-CH_2-N$ 5.9 ppm 2 protons; singlet; $-O-CH_2-O-$
6.5–9.0 ppm 17 protons; massive complex with a singlet at 8.3 ppm, aromatic protons+$N=CH-$
9–10.5 ppm 2 protons; spread peak; labile protons exchangeable with D₂O COR 01 171 solvent CDCl₃

2.3 ppm 6 protons, singlet; $N(CH_3)_2$
2.2–3.2 ppm 4 protons; massive complex; $-CH_2-CH_2-N$
5.9 ppm 2 protons; singlet; $-O-CH_2-O-$
6.6–7.5 ppm 5 protons; massive complex; aromatic protons
8.4 ppm 1 proton; singlet; $-N=CH-$ COR 01 173 solvent CDCl₃

1.6–2.1 ppm 4 protons; massive complex; $C-CH_2-CH_2-C$
2.7–3.4 ppm 8 protons; massive complex; $CH_2-CH_2-N(CH_2)_2-$
5.9 ppm 2 protons; singlet; $-O-CH_2-O-$
6.5–9.0 ppm 17 protons; massive complex with a singlet at 8.3 ppm, aromatic protons+$N=CH-$
5–11 ppm 2 protons; very spread peak; labile protons exchangeable with D₂O COR 01 174 solvent CDCl₃

1.2–2.0 ppm 6 protons; massive complex; $C-(CH_2)_3-C$
2.4–3.3 ppm 8 protons; massive complex; $CH_2-CH_2-N-(CH_2)_2$
5.9 ppm 2 protons; singlet; $-O-CH_2-O-$
6.4–9.1 ppm 17 protons; massive complex with a singlet at 8.3 ppm, aromatic protons+$-N=CH-$ 6.5–10 ppm 2 protons; very spread peak; labile protons exchangeable with D₂O

COR 01 175 solvent CDCl₃

1.3–2.0 ppm 6 protons; massive complex; C—(CH₂)₃—C
2.5–3.4 ppm 8 protons; massive complex; CH₂—CH₂—N—(CH₂)₂
5.9 ppm 2 protons; singlet; —O—CH₂—O—
6.4–7.8 ppm 16 protons; massive complex with a singlet at 8.4 ppm; aromatic protons+N=CH—
6–10 ppm 2 protons; very spread peak; labile protons exchangeable with D₂O

COR 01 176 solvent DMSO-D6

2.6 ppm 4 protons; singlet; —CH₂—C—CH₂—
2.8 ppm 6 protons; singlet; —N(CH₃)₂
2.9–3.3 ppm 4 protons; massive complex; CH₂—CH₂—N
6.0 ppm 2 protons; singlet; —O—CH₂—O—
6.9–7.9 ppm 9 protons; massive complex; aromatic protons+—CH=CH—
8.4 ppm 1 proton; doublet; —N=CH—
10.4 ppm 4 protons; large peak; labile protons exchangeable with D₂O

COR 01 179 solvent DMSO-D6

2.6 ppm 4 protons; singlet; —CH₂—C—CH₂
2.8 ppm 6 protons; singlet; N(CH₃)₂
2.9–3.3 ppm 4 protons; massive complex; CH₂—CH₂—N
6.0 ppm 2 protons; singlet; —O—CH₂—O—
6.9–7.9 ppm 5 protons; massive complex; aromatic protons
8.8 ppm 1 proton; singlet; —N=CH—
10.6 ppm 4 protons; large peak; labile protons exchangeable with D₂O

COR 01 180 solvent DMSO-D6

2.4–3.2 ppm 12 protons; massive complex; CH₂—C—CH₂+CH₂—CH₂—N(CH₂)₂
3.4–4.0 ppm 4 protons; massive complex; —CH₂—O—CH₂—
6.0 ppm 2 protons; singlet; —O—CH₂—O—
6.8–7.9 ppm 5 protons; massive complex; aromatic protons
8.7 ppm 1 proton; singlet; N=CH—
10.5 ppm 4 protons; large peak; labile protons exchangeable with D₂O

COR 01 181 solvent DMSO-D6

2.4–3.5 ppm 14 protons; massive complex; CH₂—C—CH₂+N(CH₃)₂+CH₂CH₂N—
6.0 ppm 2 protons; singlet; —O—CH₂—O—
6.8–7.6 ppm 4 protons; massive complex; aromatic protons
8.7 ppm 1 proton; singlet; N=CH—
9.5–11 ppm 4 protons; spread peak, labile protons exchangeable with D₂O

COR 01 184 solvent DMSO-D6

2.6 ppm 4 protons; singlet; —CH₂—C—CH₂—
2.7 ppm 6 protons; singlet; N(CH₃)₂
2.9–3.3 ppm 4 protons; massive complex; CH₂—CH₂—N
7.1–9.2 ppm 9 protons; massive complex with one singlet at 8.7 ppm; aromatic protons+—N=CH—
11 ppm 4 protons; large peak; labile protons exchangeable with D₂O

COR 01 185 solvent DMSO-D6

2.6 ppm 4 protons; singlet; CH₂—C—CH₂
2.7 ppm 6 protons; singlet; N(CH₃)₂
2.9–3.3 ppm 4 protons; massive complex; CH₂—CH₂—N
6.9–7.9 ppm 11 protons; massive complex; aromatic protons+—CH=CH—
8.3 ppm 1 proton; doublet; N=CH—
10.2 ppm 4 protons; dome; labile protons exchangeable with D₂O

COR 01 186 solvent DMSO-D6

1.7–2.2 ppm 4 protons; massive complex; C—CH₂—CH₂—C
2.6 ppm 4 protons; singlet; —CH₂—C—CH₂—
2.9–3.5 ppm 8 protons; massive complex; CH₂—CH₂—N(CH₂)₂
6.0 ppm 2 protons; singlet; —O—CH₂—O—
6.9–9.2 ppm 7 protons; massive complex with a singlet at 8.7 ppm; aromatic protons+N=CH
9.5–10.5 ppm 4 protons; dome; labile protons exchangeable with D₂O

COR 01 195 solvent DMSO-D6

1.3 ppm 9 protons; singlet; C(CH₃)₃
2.6 ppm 4 protons; singlet; CH₂—C—CH₂—
2.9–3.3 ppm 4 protons; massive complex; —CH₂CH₂N—
6.0 ppm 2 protons; singlet; O—CH₂—O
6.9–9.2 ppm 7 protons; massive complex with a singlet at 8.7 ppm; aromatic protons+N=CH—
9–11 ppm 5 protons; spread peak; labile protons exchangeable with D₂O

COR 01 200 solvent DMSO-D6

1.7–2.3 ppm 4 protons; massive complex; C—CH₂—CH₂—C
2.6 ppm 4 protons; singlet; CH₂—C—CH₂
2.9–3.6 ppm 8 protons; massive complex; CH₂—CH₂N(CH₂)₂
6.0 ppm 2 protons; singlet; O—CH₂—O 6.9–7.9 ppm 9 protons; massive complex; aromatic protons+—CH=CH—
8.4 ppm 1 proton; doublet; N=CH—
9.5–11 ppm 4 protons; dome; labile protons exchangeable with D₂O

COR 01 201 solvent DMSO-D6

2.6 ppm 4 protons; singlet; CH₂—C—CH₂
2.7 ppm 6 protons; singlet; N(CH₃)₂
2.9–3.2 ppm 4 protons; massive complex; CH₂CH₂N—
6.0 ppm 2 protons; singlet; O—CH₂—O
6.9–9.2 ppm 7 protons; massive complex with a singlet at 8.7 ppm; aromatic protons+N=CH—
9.5–10.5 ppm 4 protons; spread peak; labile protons exchangeable with D₂O

COR 01 202 solvent DMSO-D6

1.3—2.1 ppm 6 protons; massive complex; C—(CH₂)₃—C
2.6 ppm 4 protons; singlet; —CH₂—C—CH₂—

2.8–3.5 ppm 8 protons; massive complex; CH$_2$CH$_2$N(CH$_2$)$_2$
6.0 ppm 2 protons; singlet; —O—CH$_2$—O—
6.9—9.2 ppm 7 protons; massive complex with a singlet at 8.7 ppm; aromatic protons+—N=CH—
10 ppm 4 protons; large peak; labile protons exchangeable with D$_2$O

COR 01 203 solvent DMSO-D6

2.6 ppm 4 protons; singlet; CH$_2$—C—CH$_2$
2.7 ppm 6 protons; singlet; N—(CH$_3$)$_2$
2.8–3.3 ppm 4 protons; massive complex; CH$_2$CH$_2$N
6.0 ppm 2 protons; singlet; —O—CH$_2$—O
6.8–8.8 ppm 7 protons; massive complex with a singlet at 8.6 ppm; aromatic protons+—N=CH—
10.1 ppm 4 protons; large peak; labile protons exchangeable with D$_2$O

COR 01 204 solvent DMSO-D6

2.5–3.3 ppm 12 protons; massive complex; CH$_2$—C—CH$_2$+CH$_2$—CH$_2$N(CH$_2$)$_2$
3.4–4.0 ppm 4 protons; massive complex; CH$_2$—O—CH$_2$
6.0 ppm 2 protons; singlet; —O—CH$_2$—O—
6.9–9.2 ppm 7 protons; massive complex with a singlet at 8.7 ppm; aromatic protons+—N=CH—
10.2 ppm 4 protons; large peak; labile protons exchangeable with D$_2$O

COR 01 205 solvent DMSO-D6

2.3–3.2 ppm 19 protons; massive complex; CH$_2$—C—CH$_2$+N—CH$_3$+CH$_2$—CH$_2$—N(CH$_2$CH$_2$)$_2$
6.9–9.2 ppm 9 protons; massive complex with a singlet at 8.6 ppm; aromatic protons+—N=CH—
10.3 ppm 4 protons; large peak; labile protons exchangeable with D$_2$O

COR 01 206 solvent DMSO-D6

2.4 ppm 3 protons; singlet; CH$_3$—C
2.6 ppm 4 protons; singlet; CH$_2$—C—CH$_2$
2.7 ppm 6 protons; singlet; N(CH$_3$)$_2$
2.9–3.2 ppm 4 protons; massive complex; CH$_2$—CH$_2$N
6.0 ppm 2 protons; singlet; —O—CH$_2$—O—
6.0–8.0 ppm 6 protons; systems AA′BB′+2 singlets; aromatic protons
8.5 ppm 1 proton; singlet; N=CH—
8.5–10 ppm 4 protons; spread peak; labile protons exchangeable with D$_2$O

COR 01 207 solvent DMSO-D6

2.6 ppm 4 protons; singlet; CH$_2$—C—CH$_2$
2.8 ppm 6 protons; singlet; N(CH$_3$)$_2$
3.0–3.3 ppm 4 protons; massive complex; CH$_2$CH$_2$N
6.0 ppm 2 protons; singlet; O—CH$_2$—O 6.9–8.2 ppm 5 protons; massive complex; aromatic protons
8.6 ppm 1 proton; singlet; N=CH—
10.5 ppm 4 protons; large peak; labile protons exchangeable with D$_2$O

COR 01 208 solvent DMSO-D6

2.6 ppm 4 protons; singlet; CH$_2$—C—CH$_2$
2.7 ppm 6 protons; singlet; N(CH$_3$)$_2$
2.9–3.2 ppm 4 protons; massive complex; CH$_2$CH$_2$N
6.0 ppm 2 protons; singlet; O—CH$_2$—O
6.9–8.1 ppm 6 protons; system AA′BB′+2 singlets; aromatic protons
8.6 ppm 1 proton; singlet; N=CH—
8–10 ppm 4 protons; spread peak; labile protons exchangeable with D$_2$O

COR 01 209 solvent CMSO-D6

2.6 ppm 4 protons; singlet; CH$_2$—C—CH$_2$
2.7 ppm 6 protons; singlet; N(CH$_3$)$_2$
2.9—3.2 ppm 4 protons; massive complex; CH$_2$—CH$_2$—N
6.0 ppm 2 protons; singlet; O—CH$_2$—O
6.9—8.1 ppm 7 protons; massive complex; aromatic protons
8.6 ppm 1 proton; singlet; N=CH—
9.8 ppm 4 protons; large peak; labile protons exchangeable with D$_2$O

COR 01 210 solvent DMSO-D6

2.6 ppm 4 protons; singlet; CH$_2$—C—CH$_2$
2.7 ppm 6 protons; singlet; N(CH$_3$)$_2$
2.9–3.3 ppm 4 protons; massive complex; CH$_2$CH$_2$N
3.8 ppm 3 protons; singlet; OCH$_3$
6.0 ppm 2 protons; singlet; O—CH$_2$13 O
6.7–8.0 ppm 6 protons; massive complex; aromatic protons
8.5 ppm 1 proton; singlet; N=CH—
9.9 ppm 4 protons; large peak; labile protons exchangeable with D$_2$O

COR 01 213 solvent DMSO-D6

1.3 ppm 3 protons; doublet; CH$_3$—C
2.4–4.2 ppm 13 protons; massive complex; CH$_2$—C—CH$_2$+N (CH$_3$)$_2$+CHCH$_2$—N
7.1–9.2 ppm 9 protons; massive complex with a singlet at 8.7 ppm, aromatic protons+—N=CH—
10.6 ppm 4 protons; large peak; labile protons exchangeable with D$_2$O

COR 01 214 solvent DMSO-D6

1.1 ppm 3 protons; doublet; CH$_3$—C—
2.4–3.8 ppm 13 protons; massive complex; CH$_2$—C—CH$_2$+N(CH$_3$)$_2$+CH$_2$—CH—N—
7.0–9.2 ppm 9 protons; massive complex with a singlet at 8.7 ppm; aromatic protons+N=CH—
10.5 ppm 4 protons; large peak; labile protons exchangeable with D$_2$O 2. Elementary micro analysis

| Product No. (COR) | CARBON | | HYDROGEN | | NITROGEN | | OXYGEN | |
|---|---|---|---|---|---|---|---|---|
| | Theor | Actual | Theor | Actual | Theor | Actual | Theor | Actual |
| 01 151 | 67.90 | 67.10 | 5.70 | 5.88 | 5.28 | 4.89 | 15.08 | 14.54 |
| 01 169 | 68.36 | 69.17 | 5.92 | 6.27 | 5.14 | 4.95 | 14.69 | 14.01 |
| 01 170 | 70.84 | 70.94 | 5.95 | 5.96 | 7.99 | 8.18 | 15.22 | 15.68 |
| 01 173 | 71.85 | 71.08 | 6.03 | 6.49 | 7.62 | 7.46 | 14.50 | 13.95 |
| 01 174 | 72.19 | 72.07 | 6.24 | 6.16 | 7.43 | 7.42 | 14.14 | 13.75 |

2. Elementary micro analysis

| Product No. (COR) | CARBON Theor | Actual | HYDROGEN Theor | Actual | NITROGEN Theor | Actual | OXYGEN Theor | Actual |
|---|---|---|---|---|---|---|---|---|
| 01 175 | 69.45 | 69.26 | 6.00 | 6.00 | 4.91 | 4.77 | 14.02 | 13.68 |
| 01 176 | 60.69 | 59.90 | 5.88 | 5.84 | 5.44 | 5.35 | 27.99 | 27.88 |
| 01 179 | 53.45 | 53.15 | 5.30 | 5.84 | 5.66 | 4.92 | 29.12 | |
| 01 181 | 46.08 | 46.25 | 4.39 | 4.65 | 4.89 | 4.31 | 25.11 | 25.59 |
| 01 185 | 63.82 | 64.08 | 6.43 | 6.70 | 5.95 | 5.85 | 23.80 | 23.18 |
| 01 195 | 58.02 | 58.88 | 6.04 | 6.73 | 8.12 | 7.87 | 27.82 | 28.17 |
| 01 200 | 62.21 | 62.93 | 5.97 | 6.46 | 5.18 | 4.74 | 26.64 | 26.59 |
| 01 201 | 56.44 | 56.67 | 5.56 | 5.95 | 8.58 | 8.54 | 29.42 | 30.25 |
| 01 203 | 54.65 | 54.90 | 5.38 | 5.59 | 8.31 | 8.17 | 31.65 | |
| 01 204 | 56.49 | 56.60 | 5.50 | 5.67 | 7.91 | 7.36 | 30.10 | 29.85 |
| 01 205 | 59.99 | 59.59 | 6.44 | 6.50 | 11.19 | 10.56 | 22.37 | |
| 01 206 | 59.75 | 59.77 | 6.02 | 6.17 | 5.57 | 5.33 | 28.66 | 29.62 |
| 01 207 | 51.72 | 51.88 | 4.70 | 5.17 | 5.03 | 4.67 | 25.83 | 25.02 |
| 01 208 | 55.12 | 55.25 | 5.20 | 5.54 | 5.36 | 4.90 | 27.54 | 27.33 |
| 01 209 | 59.00 | 58.98 | 5.78 | 6.08 | 5.73 | 5.17 | 29.48 | 29.66 |

The products of this invention were submitted to various pharmacological tests which produced the following results.

The mortality percentages caused by the products of the present invention administered orally to Swiss mice are shown in Table 1. The animals, free of specific pathological organism were housed in an air conditioned room from 24 to 48 hours before the start of the experiments. They were divided up into lots of 5 males and 5 females. With the animals unfed for 24 hours, the substances were administered intragastrically in a base of 6% gum arabic in a volume equal to 0.1 ml for 10 g of animal weight. The mortality was recorded at 14 days.

The analgesic activity was determined with the male Swiss mouse using phenylbenzoquinone (PBQ) (a variation of the method of Siegmund et al, Proc. Soc. Exp. Med., 1975, 95, 729-31) as the noxious agent. Twenty-eight minutes after having administered the test products in a suspension in a 6% gum base, the PBQ solution was injected. The mice were then observed ca. 5 mn. for the next five minutes. The results are shown in Table 2.

The psychotropic profile of the present invention products has been characterized with the animals in numerous tests some of whose results are shown hereinafter. The products of the invention were always administered orally in 6% gum base. Table 3 shows the effect induced in the escape test with the mouse and expressed by the percentages of variation of the number of escapes the animal made in 5 minutes.

TABLE 1

Toxicity with the Mouse

% of mortality as a function of the dose administered in mg/kg

| Product No. | 150 | 250 | 500 | 750 | 1000 | 1500 | 2000 |
|---|---|---|---|---|---|---|---|
| COR 01 142 | | | | | 0 | | 50 |
| COR 01 151 | 0 | 10 | 40 | 60 | | | |
| COR 01 163 | 25 | 70 | 100 | | | | |
| COR 01 169 | | | | 50 | 20 | 80 | |
| COR 01 170 | | | | | 0 | 100 | |
| COR 01 171 | 20 | 80 | 90 | | | | |
| COR 01 173 | | | 0 | | 30 | | |
| COR 01 174 | | | 0 | | 10 | | 50 |
| COR 01 175 | | | 0 | 10 | 10 | | |
| COR 01 176 | | | | | 0 | | |
| COR 01 179 | | 10 | 90 | | | | |
| COR 01 180 | | | 0 | | 70 | | |
| COR 01 181 | | 0 | 30 | | | | |

TABLE 1-continued

Toxicity with the Mouse

% of mortality as a function of the dose administered in mg/kg

| Product No. | 150 | 250 | 500 | 750 | 1000 | 1500 | 2000 |
|---|---|---|---|---|---|---|---|
| COR 01 184 | | | | | | 0 | 30 |
| COR 01 185 | | | | | | 0 | 100 |
| COR 01 186 | | | 0 | 40 | 50 | | |
| COR 01 195 | | | | | 0 | 20 | 30 |
| COR 01 199 | | | | | 0 | | 50 |
| COR 01 200 | | | 0 | 10 | 70 | | |
| COR 01 201 | | | | 10 | | | 30 |
| COR 01 202 | | 10 | 30 | 60 | | | |
| COR 01 203 | | | | 0 | 10 | | 40 |
| COR 01 204 | | | | | 0 | | 10 |
| COR 01 205 | | | | 0 | 10 | | 10 |
| COR 01 206 | | | | | 0 | | 50 |
| COR 01 207 | | | | 0 | 20 | 20 | 40 |
| COR 01 208 | | 0 | 30 | 20 | 20 | | 80 |
| COR 01 209 | | | | | 0 | 40 | 60 |
| COR 01 210 | | | | 0 | 10 | | 20 |
| COR 01 213 | | | | | | | 0 |
| COR 01 214 | | | | | 0 | 30 | 70 |

TABLE 2

% of analgesic activity as a function of the dose expressed in mg/kg

| Product No. | 50 | 100 | 200 |
|---|---|---|---|
| COR 01 142 | 22 | 20 | 10 |
| COR 01 151 | 41 | 79 | |
| COR 01 163 | 17.5 | | |
| COR 01 169 | 7 | 43 | |
| COR 01 170 | | 30 | 39 |
| COR 01 171 | 51 | | |
| COR 01 174 | | 48 | 18 |
| COR 01 175 | | 13 | 71 |
| COR 01 176 | | 23 | 39 |
| COR 01 180 | 18 | 26 | 34 |
| COR 01 181 | 25 | 42 | |
| COR 01 184 | 34 | 44 | 55 |
| COR 01 195 | | 24 | 31 |
| COR 01 199 | 8 | 24.5 | 56.5 |
| COR 01 202 | 2 | 0 | 33 |
| COR 01 203 | 0 | 36 | 47 |
| COR 01 204 | 0 | 45 | 42 |
| COR 01 205 | | 10 | 36 |
| COR 01 209 | | | 17 |
| COR 01 210 | | 27 | 33 |
| COR 01 214 | | 21 | 30 |
| Acetylsalicyclic acid | | 55 | 61 |

TABLE 3

Escape Test

% of activity as a function of the dose expressed in mg/kg

| Product No. | 0.5 | 1 | 3 | 5 | 10 | 25 | 50 | 75 | 100 | 150 | 200 |
|---|---|---|---|---|---|---|---|---|---|---|---|
| COR 01 151 | | | | | | NS | NS | NS | −41 | | |
| COR 01 170 | | | | | | | NS | NS | −32 | | −59 |
| COR 01 173 | | | | −33 | | −13 | −29 | −26 | −50 | −55 | −90 |
| COR 01 176 | −29 | −40 | −39 | −33 | | −32 | −37 | | −33 | | −43 |
| COR 01 180 | | | | NS | NS | NS | −21 | | −37 | | −75 |
| COR 01 184 | | | | −34 | −26 | −23 | −34 | | −47 | | −46 |
| COR 01 195 | NS | NS | +54 | +53 | NS | NS | +19 | | +28 | | NS |
| COR 01 200 | | | | NS | +25 | NS | +38 | NS | NS | | |
| COR 01 202 | | NS | | NS | NS | NS | NS | NS | | | |
| COR 01 203 | | | | NS | | NS | NS | | NS | | |
| COR 01 204 | | | | −28 | NS | −31 | −24 | −20 | −15 | | −24 |
| COR 01 205 | | | | NS | | NS | NS | NS | | | −34 |
| COR 01 206 | | | | | NS | −18 | −28 | | −63 | | |
| COR 01 209 | | | | −28 | | −38 | −32 | | −37 | | −20 |
| COR 01 210 | | | | NS | | NS | NS | | −20 | −26 | −72 |
| COR 01 213 | | NS | | NS | | | NS | −20 | NS | | |
| COR 01 214 | | NS | | NS | | | NS | | | | |

The notation NS signifies that the difference between the results noted for the product and the results noted for the excipient alone is not significant at the threshold 0.05 according to the Student t Test.

The products of the present invention do not in general show any cataleptic activity in strong dosage. Only COR 01 176 brought about a slight catalepsy at 400 and 600 mg/kg. Certain derivatives manifest an antagonism vis-a-vis the stereotype with apomorphine: i.e., COR 01 176, 202, 206, 209, and 210.

The results of this test are shown in Table 4.

TABLE 4

% of activity vis-a-vis the stereotype induced by apomorphine as a function of the administered dose expressed in mg/kg

| Product No. | 25 | 50 | 75 | 100 | 150 | 200 |
|---|---|---|---|---|---|---|
| COR 01 176 | | | | | | −64 |
| COR 01 202 | −35 | −32 | −29 | NS | | −20 |
| COR 01 206 | NS | −53 | | −71 | | −22 |
| COR 01 209 | | −54 | | −51 | | −42 |
| COR 01 210 | | | −33 | | −33 | |

An inhibition test of the group toxicity induced by amphetamine makes it possible to reject the hypothesis of neuroleptic activity for these derivatives.

A certain number of products manifest an anxiolytic activity evidenced in the test with the four plates with the mouse (Table 5).

TABLE 5

% of increase in the number of displacements of the animal as a function of the dose expressed in mg/kg

| Product No. | 1.5 | 3 | 5 | 10 | 20 | 25 | 40 | 50 | 60 | 75 |
|---|---|---|---|---|---|---|---|---|---|---|
| COR 01 170 | | | | | | +18 | +57 | +36 | +69 | +72 |
| COR 01 173 | | | NS | +30 | +47 | | | +60 | | +82 |
| COR 01 176 | NS | +101 | +117 | +72 | +72 | +66 | | NS | | |
| COR 01 180 | | | NS | NS | | +69 | | +88 | | +35 |
| COR 01 184 | +89 | +73 | +56 | +61 | | NS | | | | |
| COR 01 200 | | | +112 | +180 | +292 | +142 | | +84 | | |
| COR 01 202 | | | | | | +48 | | +96 | | |

Certain tests made it possible to show antidepressive activities. These are tests of antagonism to the effects of reserpine, oxotremorine (according to Everett G. M. et al, Science, 1956, 124, 79 and Levy J. et al, Therapie 1965, 20, 265) and to despair (according to Porsolt P. D. et al, Eur. J. Pharmacol., 1978, 47, 379-91). These results are shown in Tables 6, 7 and 8.

TABLE 6

% of inhibition of ptosis induced by reserpine as a function of the dose administered orally expressed in mg/kg

| Product No. | 2.5 | 5 | 10 | 25 | 50 | 75 | 100 | 200 |
|---|---|---|---|---|---|---|---|---|
| COR 01 173 | | | | | −12 | −21 | −23 | |
| COR 01 180 | −18 | −34 | −26 | −20 | NS | | | |
| COR 01 184 | | | | | −13 | | −39 | −34 |
| COR 01 195 | | | | NS | −22 | | −22 | |
| COR 01 200 | | | NS | −28 | NS | | −24 | |
| COR 01 203 | | | | | NS | | −33 | −27 |
| COR 01 205 | | | | NS | −31 | | −25 | −31 |
| COR 01 209 | | | | | | | NS | −45 |
| COR 01 210 | | | | NS | −21 | | −38 | |

TABLE 7

% of inhibition of trembling induced by oxotremorine as a function of the dose administered expressed in mg/kg

| Product No. | 25 | 50 | 75 | 100 | 150 | 200 |
|---|---|---|---|---|---|---|
| COR 01 170 | | −40 | | −50 | | −78 |
| COR 01 173 | −20 | −20 | −40 | −60 | −70 | |
| COR 01 176 | | −40 | | −50 | | −20 |
| COR 01 180 | | −22 | | −44 | | −44 |
| COR 01 184 | −20 | 0 | | −22 | | −17 |
| COR 01 202 | 0 | −67 | −44 | | | |
| COR 01 203 | | −70 | | −50 | | −20 |
| COR 01 204 | | −30 | | −20 | | −30 |
| COR 01 205 | | −30 | | −30 | | −40 |
| COR 01 209 | | −60 | −60 | −55 | −60 | −30 |
| COR 01 210 | | −50 | −40 | −50 | −30 | −50 |

TABLE 8

| | Test of despair: % of antagonism as a function of the dose administered orally and expressed in mg/kg | | |
|---|---|---|---|
| Product No. | 50 | 100 | 200 |
| COR 01 170 | −39 | −39 | −33 |
| COR 01 173 | −18 | −41 | −53 |
| COR 01 184 |  | −20 | −18 |
| COR 01 202 | −49 | −67 |  |

None of the products tested showed any activity in the 5 HTP test; the derivatives forming the object of the present invention, thus, have no inhibiting effect on the monoamine oxydase.

Certain products manifest an anticholinergic activity evidenced in the inhibition test of salivation induced by pilocarpine (Table 9).

TABLE 9

| | % of inhibition of salivation induced by pilocarpine as a function of the dose administered expressed in mg/kg | | | |
|---|---|---|---|---|
| Product No. | 50 | 75 | 100 | 200 |
| COR 01 170 | NS |  | −18 | −57 |
| COR 01 173 | NS | −39 | −48 | −76 |
| COR 01 184 |  |  |  | −23 |
| COR 01 203 | −32 |  | NS | −30 |

Doses and therapeutic schedules will be a function of the subject. As a general rule, they initiate a progressive posology and progressively arrest treatment. The products forming the object of the present invention may be administered orally, (e.g., in the form of capsules, compressed tablets, drinkable drops) or by injection (injectable solution for intramuscular or intravenous administration; intravenous perfusion administration). Generally, an amount effective to induce central nervous system activity, e.g., antidepressant, anxiolytic, or analgesic activity, is combined with a pharmaceutically acceptable diluent or carrier. The daily dose can usually be varied from 3 to 300 mg in one to three doses. Non-limiting examples of such formulations are set forth below.

| | |
|---|---|
| Drinkable drops | |
| COR 01 176 | 0.6 grams of base per 30 ml bottle to produce about 0.5 mg per drop |
| Tablets | |
| COR 01 184 | tablets of 25 mg base |
| COR 01 173 | tablets of 100 mg base |
| COR 01 202 | tablets of 5 mg base |
| Injectable solutions | |
| COR 01 202 | ampullae injectable doses of 25 mg base |
| COR 01 184 | ampullae injectable doses of 25 mg base |

Having now fully described this invention, it will be apparent to one of ordinary skill in the art that many changes and modifications can be made thereto without departing from the spirit or scope of the invention set forth herein.

What is claimed is:

1. A compound of the formula

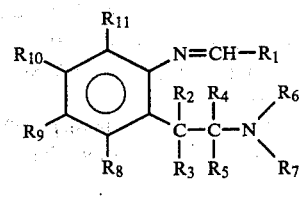

wherein $R_1$ is phenyl which is unsubstituted or substituted by at least one member selected from the group consisting of halogen, $CF_3$, $C_1$-$C_4$ alkyl, $C_1$-$C_4$ alkoxy and COOH, or $R_1$ is

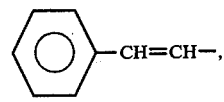

or $R_1$ is a heterocycle selected from the group consisting of

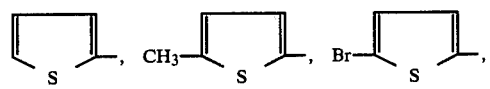

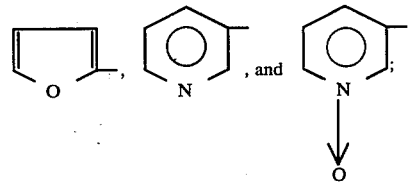

$R_2$, $R_3$, $R_4$ and $R_5$, which may be identical or different, are H or $CH_3$;

$R_6$ and $R_7$, which may be identical or different, are $C_1$-$C_6$ alkyl, which may be straight-chained or branched, or $R_7$ can be H when $R_6$ is a branched-chain alkyl, or $R_6$ and $R_7$ can form, with the nitrogen to which they are bonded, a heterocycle selected from the group consisting of

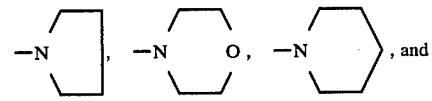

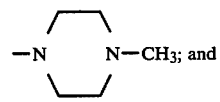

$R_8$, $R_9$, $R_{10}$ and $R_{11}$, which may be identical or different, are H, halogen, $CF_3$, hydroxy or $C_1$-$C_4$ alkoxy, or two contiguous members of $R_8$, $R_9$, $R_{10}$ and $R_{11}$ may together form a chain —O—$(CH_2)_n$—O—, where n=1 or 2, or a chain —O—$CH_2$—O—$CH_2$—;

or a pharmaceutically acceptable addition salt thereof.

2. The compound according to claim 2, wherein the pharmaceutically acceptable acid addition salt is the salt of chlorhydric acid, benzilic acid or citric acid.

3. The compound according to claim 1 or 2, wherein $R_8 = R_9 = R_{10} = R_{11} = H$.

4. The compound according to claim 1 or 2, wherein $R_8 = R_{11} = H$ and $R_9 + R_{10}$ together form a chain $-O-CH_2-O-$.

5. A composition exhibiting central nervous system activity comprising
   in an amount effective to exhibit central nervous system activity the compound according to claim 1 or 2, and
   a pharmaceutically acceptable diluent or carrier.

6. A composition exhibiting central nervous system activity comprising
   in an amount effective to exhibit central nervous system activity the compound according to claim 3, and
   a pharmaceutically acceptable diluent or carrier.

7. A composition exhibiting central nervous system activity comprising
   in an amount effective to exhibit central nervous system activity the compound according to claim 4, and
   a pharmaceutically acceptable diluent or carrier.

* * * * *